United States Patent
Greenhut et al.

[11] Patent Number: 5,720,295
[45] Date of Patent: Feb. 24, 1998

[54] PACEMAKER WITH IMPROVED DETECTION OF ATRIAL FIBRILLATION

[75] Inventors: Saul E. Greenhut, Aurora; Tibor A. Nappholz, Englewood, both of Colo.

[73] Assignee: Pacesetter, Inc., Sylmar, Calif.

[21] Appl. No.: 730,748

[22] Filed: Oct. 15, 1996

[51] Int. Cl.$^6$ .......................... A61B 5/0452; A61N 1/362
[52] U.S. Cl. .................. 128/704; 607/5; 607/9
[58] Field of Search .................. 128/702, 704, 128/705; 607/4, 5, 9, 26

[56] References Cited

U.S. PATENT DOCUMENTS

| | | |
|---|---|---|
| 4,702,253 | 10/1987 | Nappholz et al. |
| 4,766,901 | 8/1988 | Callaghan. |
| 4,901,725 | 2/1990 | Nappholz et al. |
| 5,201,808 | 4/1993 | Steinhaus et al. |
| 5,240,009 | 8/1993 | Williams .................. 128/702 |
| 5,423,868 | 6/1995 | Nappholz et al. |
| 5,441,523 | 8/1995 | Nappholz. |
| 5,454,836 | 10/1995 | van der Veen et al. ............ 607/9 |

*Primary Examiner*—William E. Kamm
*Assistant Examiner*—George R. Evanisko
*Attorney, Agent, or Firm*—Gottlieb, Rackman & Reisman

[57] ABSTRACT

In a dual chamber implantable pacemaker, the peak amplitude of the atrial intrinsic signals are monitored and used to generate a short term and a long term indicia indicative of the intrinsic signals' variability and deviation from normal sinus rhythm peak amplitudes. The two indicia are combined to generate a single indicia which is then used to categorize the state of the atrium as one of several conditions such as flutter/flubber, coarse atrial fibrillation or fine atrial fibrillation. The categorization is used by a microcontroller for generating the proper pacing pulses and may also be used as a criteria for mode switching between a first mode wherein synchrony between the atrium and ventricle is maintained and a second mode pacing is performed at a fixed rate or one determined by the metabolic indicator.

17 Claims, 8 Drawing Sheets

SINUS RHYTHM

FIG. 5A

REGULAR SUPRAVENTRICULAR ARRHYTHMIA

FIG. 5B

ATRIAL FLUTTER / FIBRILLATION

PACEMAKER WITH IMPROVED DETECTION OF ATRIAL FIBRILLATION

BACKGROUND OF THE INVENTION

A. Field of Invention

This invention pertains to pacemakers in which the atrial rhythm is categorized using statistical analysis of its amplitude and its rate in relation to a physiological parameter. It also pertains to implantable cardioverter-defibrillators and atrial defibrillators for rhythm classification. Once the atrial condition is established, a decision can be made as to whether and what type of atrial and/or ventricular therapy is desirable (if any).

B. Description of the Prior Art

The primary function of a pacemaker (cardiac pulse generator) is to sense for intrinsic (natural) events, that is, P-waves and R-waves, and if such are absent to provide stimulation or pacing pulses in either or both the atrium and the ventricle.

A dual chamber pacemaker stimulates a patient's heart in the most physiologically efficient manner when it provides atrioventricular (AV) synchrony. This means that each atrial contraction (P-wave) is followed, after an appropriate AV delay, by a ventricular contraction (R-wave), which is the sequence exhibited by a healthy heart.

In a dual chamber pacemaker, the rate of ventricular pacing pulses (V-pace) which are provided in the absence of sensed intrinsic ventricular activity (V-sense) is determined by the atrial channel. The atrial channel may either sense a P-wave (A-sense) or, in the absence of an A-sense, provide a pacing pulse (A-pace). When the atrial channel senses a P-wave, the ventricular channel follows, one for one, providing a pacing pulse (V-pace) in the absence of a V-sense. This provides the intended therapy of increased hemodynamic output with increased sinoatrial rate.

The dual chamber pacemaker must also cope with atrial tachyarrhythmia and the mechanism to do this is the "programmed maximum rate." This maximum rate is usually the upper rate limit both (i) when the ventricular channel is tracking (or following) A-senses in the atrial channel, and (ii) when in the case of a sensor driven, rate responsive pacemaker, the atrial channel is pacing, i.e., providing A-paces. A rate responsive pacemaker has an independent sensor which measures a physical or metabolic parameter. The sinus rate is combined with the sensor indicated rate to determine the atrial pacing rate. This also has the effect of providing increased hemodynamic output for a patient who has sinus node disease.

State-of-the-art pacemakers have automatic mode switching (AMS) which allow the pacing mode to change from an atrial tracking (following) mode to a non-atrial tracking mode upon sensing an elevated atrial rate (see for example U.S. Pat. No. 5,441,523).

The time period between an atrial and a subsequent ventricular pace, (the A-V delay) is one of the parameters that is set in the pacemakers as part of their normal operation. During this A-V delay, the atrio-ventricular valve is open and the blood flows from atrium through this valve into the ventricle. At the end of the A-V delay, a ventricular pacing pulse initiates a contraction which closes the A-V valves and opens the aortic and pulmonary valves to cause blood to flow into the arteries. The amount of blood delivered into the ventricles and eventually by the heart to the arteries, i.e., the stroke volume for each heart beat, is dependent on both the A-V delay and the physiological characteristics of the heart, which characteristics are unique for each patient.

A problem in these types of pacemakers has been that, due to the low amplitudes of the intrinsic atrial signals, it is difficult to analyze the same to determine the status of the atrial condition and hence affect behavior of the implanted device. The behavior of the device in response to detection of a pathological atrial rhythm might consist of AMS, anti-tachycardia pacing, cardioversion, or defibrillation.

OBJECTIVES AND SUMMARY OF THE INVENTION

It is an objective of the present invention to provide a novel means of classifying the cardiac condition of a patient using statistical information obtained from the atrium over a preselected time period.

Another object is to provide a means of further classifying the cardiac condition based on information obtained from a metabolic sensor.

A further objective is to provide in an implantable cardiac device such as a dual chamber pacemaker, an implantable cardioverter/defibrillator or an atrial defibrillator means of correctly determining and classifying the condition of a patient's atrium for diagnosis and treatment.

Yet another objective is to provide a pacemaker with an atrial state determination using a relatively simple method which is easy to implement. Other objectives and advantages of the invention shall become apparent from the following description.

Briefly, the present inventors have discovered that intrinsic atrial rhythms are characterized by amplitude variations which define patterns unique to specific atrial arrhythmia. Therefore, by statistically analyzing these variations, the atrial arrhythmia can be classified. More specifically, atrial signals can be classified into one of five categories as follows:

I. Sinus Rhythm;

II. Regular supraventricular arrhythmia;

III. Atrial fibrillation or flutter/fibrillation (flubber);

IV. Noise, usually due to electromagnetic interference; and

V. Retrograde atrial activation.

Category IV is not well suited for the analysis disclose herein and therefore it is not discussed further. Category V, retrograde atrial activation, may cause pacemaker mediated tachycardia (PMT). A means of identifying PMT is disclosed in commonly assigned U.S. Pat. No. 5,423,868 and incorporated herein by reference.

Briefly, the present pacemaker constructed in accordance with this invention includes means for sensing atrial signals, means for analyzing these signals to determine their peak amplitudes of a plurality of consecutive signals, and means for analyzing these peak amplitudes statistically so that the atrial status can be categorized. It may optionally include means for measurement of a metabolic sensor which provides information on the appropriateness of the intrinsic atrial rate and whether said rate is pathological.

3

DETAILED DESCRIPTION OF THE INVENTION

A pacemaker incorporating the present invention is shown in FIGS. 1–4. Except for the features covering the determination of atrial amplitude, the pacemaker of these Figures is constructed and operates in accordance with the description found in commonly assigned U.S. Pat. No. 5,441,523 by Tibor A. Nappholz, entitled FORCED ATRIOVENTRICULAR SYNCHRONY DUAL CHAMBER PACEMAKER, incorporated herein by reference.

Figure 1:
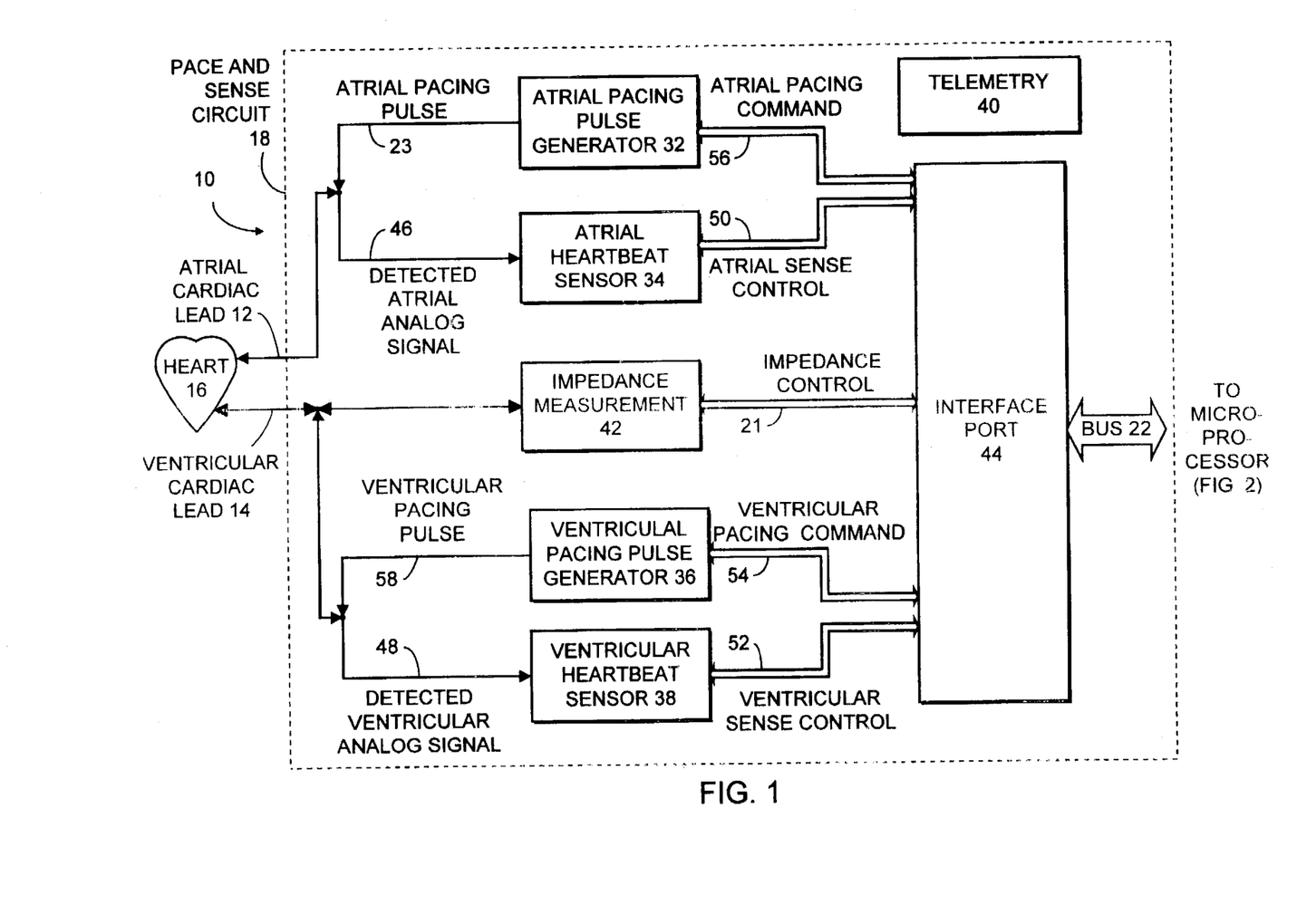
FIG. 1 shows a block diagram of a sensing/pacing section of a pacemaker Constructed in accordance with this invention.

Briefly, the pacemaker 10 shown in FIG. 1 is designed to be implanted in a patient and is connected by leads 12 and 14 to a patient's heart 16 for sensing and pacing the same. The atrial cardiac lead 12 extends into the atrium of the heart 16 and the ventricular cardiac lead 14 extends into the ventricle of the heart 16. Other lead configurations are possible, including the inclusion of additional leads sensing atrial signals and/or the absence of a ventricular lead in, for example, an atrial antitachycardia pacemaker. Leads 12 and 14 are used for both sensing electrical activity in the heart and for applying pacing pulses to the heart. The pacemaker 10 includes a pace and sense circuit 18 for the detection of analog signals from leads 12 and 14 and for the delivery of pacing pulses to the heart. A microprocessor 20 (FIG. 2) is also provided, in response to inputs received from the pace and sense circuit 18, performs operations to generate different control and data outputs to the pace and sense circuit 18. A power supply (not shown) provides voltage to the pace and sense circuit 18 and the microprocessor 20.

Figure 2:
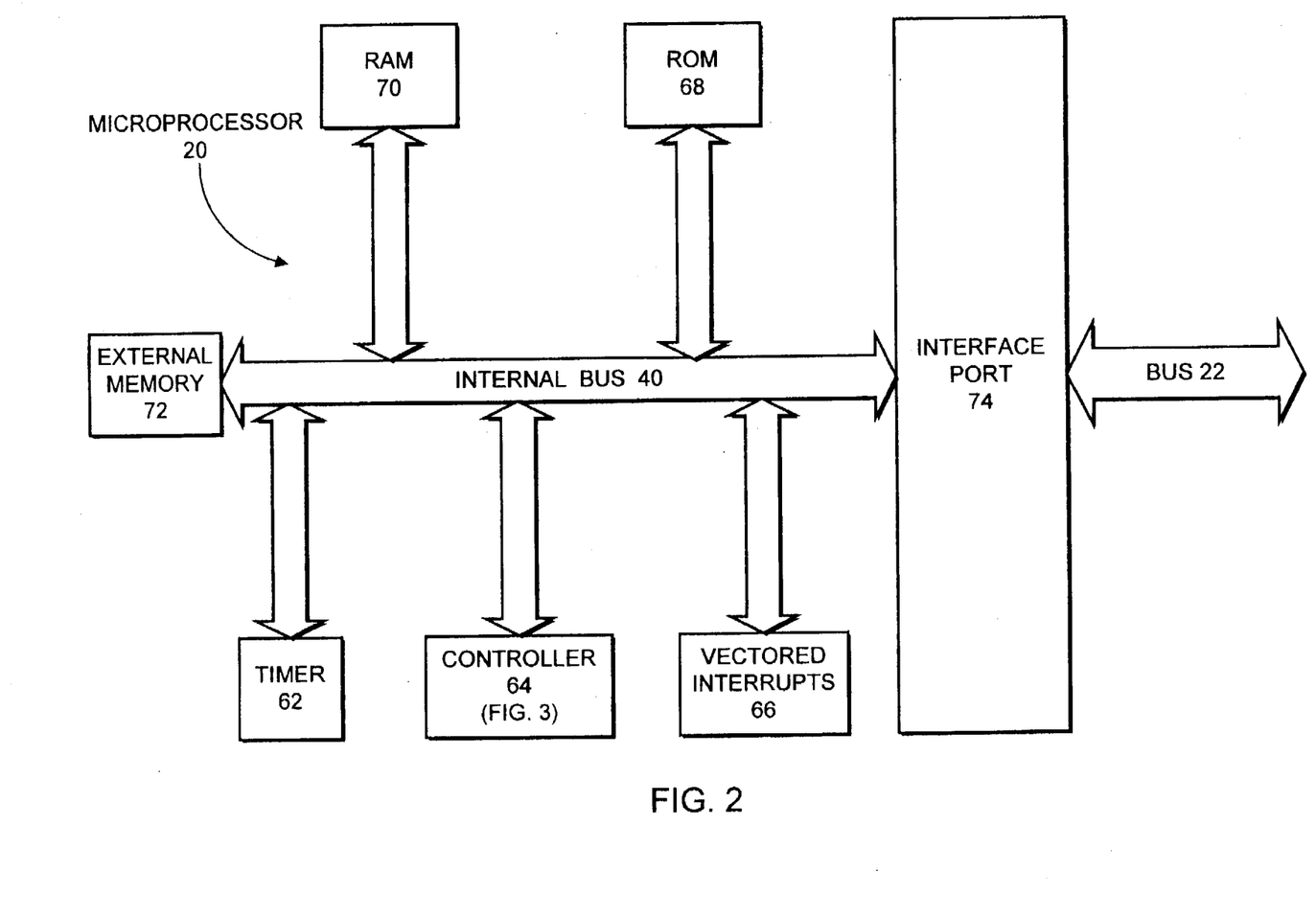
FIG. 2 shows a block diagram of the microprocessor for a pacemaker constructed in accordance with this invention.

The microprocessor 20 and the pace and sense circuit 18 are connected to each other by a number of data and control lines included in bus 22.

FIG. 1 further shows details of the pace and sense circuit 18. The circuit 18 includes an atrial pacing pulse generator 32, a ventricular pacing pulse generator 36, an atrial heartbeat sensor 34, a ventricular sensing circuit 38, and a telemetry circuit 40. The preferred embodiment of the pace and sense circuit 18 also includes an impedance measurement circuit 42 for measuring a respiratory parameter indicative of the patient's metabolic demand as described in detail in U.S. Pat. No. 4,901,725 and incorporated herein by reference. The pace and sense circuit 18 also includes a interface port 44 for interfacing with the microprocessor 20 via bus 22.

In operation, the atrial and ventricular sensing circuits 34 and 38 detect respective atrial and ventricular analog signals 46 and 48 from the heart 16 and convert the detected analog signals to digital signals.

The atrial pacing pulse generator circuit 32 receives via microprocessor 20 and interface port 44 on bus 56, an atrial pace command to generate an atrial pacing pulse 23 at appropriate times. Similarly, the ventricular pacing pulse generator circuit 36 receives from the interface port 44, and control bus 54, a ventricular pace command to generate a ventricular pacing pulse 58.

The telemetry circuit 40 provides a bidirectional link between the interface port 44 of the pace and sense circuit 18 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

FIG. 2 shows the microprocessor 20 having a timer circuit 62 for generating several timing signals, a controller 64, a vectored interrupts circuit 66, a ROM 68, a RAM 70, an external memory 72 and an interface port 74. Signals between these elements are exchanged via an internal communications bus 40. The RAM 70 acts as a scratchpad and active memory during execution of the programs stored in the ROM 68 and used by the microprocessor 20. ROM 68 is used to store various subroutines.

The microprocessor 20 through its interface port 74 receives status inputs from the pace and sense circuit 18. Using controller 64, it performs various operations, including arrhythmia detection, and produces commands, such as the atrial pace command on the bus 56 and the ventricular pace command on the bus 54, which determine the type of pacing that is to take place.

The pacemaker 10 of the present invention will function properly using any metabolic indicator rate system, so long as that system is able to reliably relate the sensed parameter to a metabolic demand pacing rate. For example, U.S. Pat. No. 4,766,901, to F. Callaghan, issued Aug. 30, 1988, for "Rate Responsive Pacing System Using the Integrated Evoked Potential," refers to the operation of a rate-responsive pacing system using an integrated evoked ventricle depolarization potential (or PDI) as a metabolic demand pacing rate indicator. U.S. Pat. No. 4,702,253 to T. A. Nappholz et al., issued Oct. 27, 1987, for "Metabolic-Demand Pacemaker and Method of Using the Same to Determine Minute Volume," U.S. Pat. No. 4,901,725, to T. A. Nappholz et at., issued Feb. 20, 1990 for "Minute Volume Rate-Responsive Pacemaker", and U.S. Pat. No. 5,201,808 to B. M. Steinhaus et al., entitled "Minute Volume Rate-Responsive Pacemaker Employing Impedance Sensing on a Unipolar Lead", which issued on Apr. 13, 1993, disclose rate-responsive pacers describing another metabolic demand pacing rate indicator, respiratory minute volume, as the rate control parameter. The pacemaker 10 can employ any rate response techniques available or no rate response at all. The preferred embodiment of the invention employs the impedance measurement circuit 42 which measures the thoracic impedance to determine the respiratory minute volume in accordance with the '725 Nappholz patent mentioned above.

Figure 3:
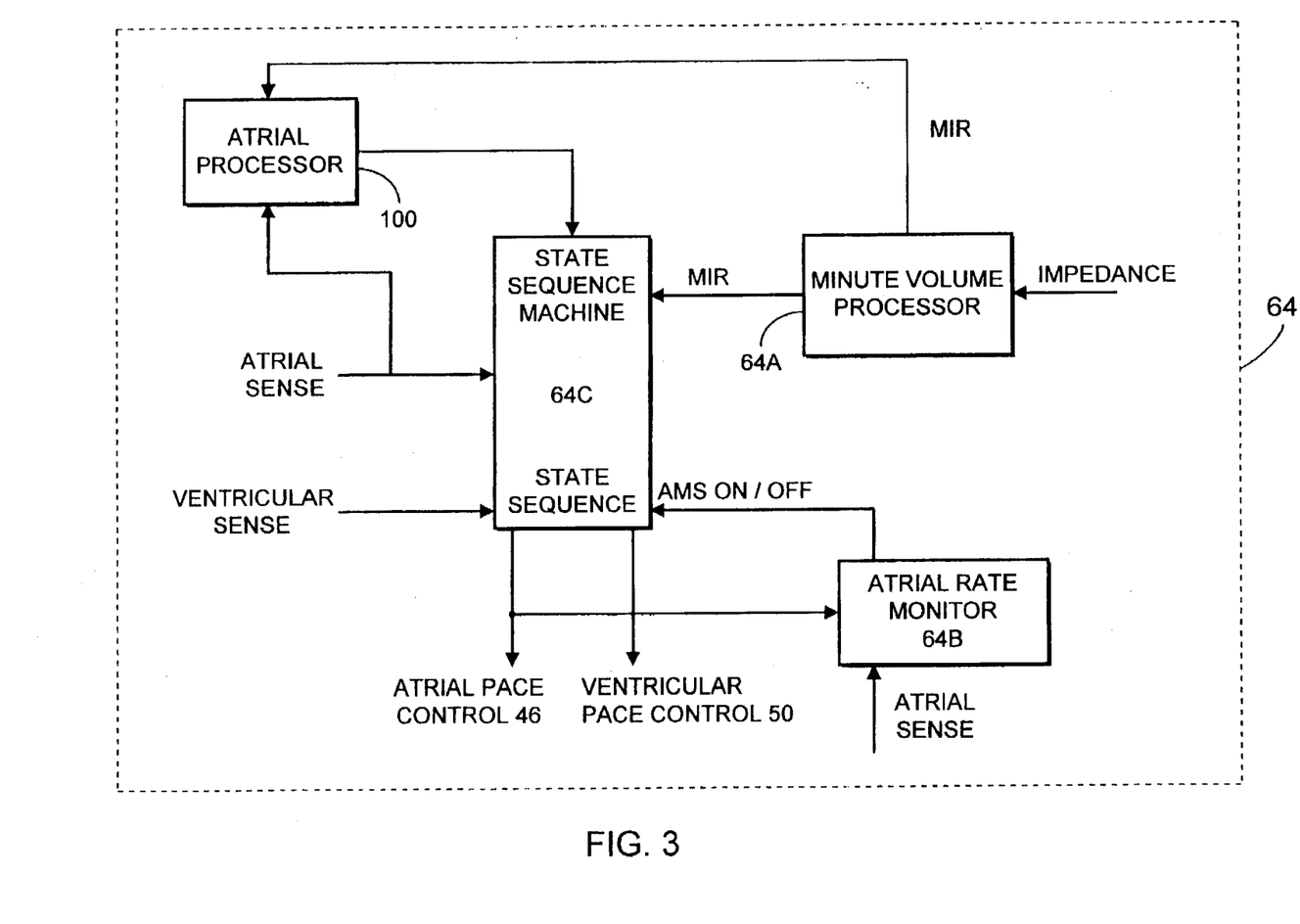
FIG. 3 shows details of the controller of the microprocessor of FIG. 2.

FIG. 3 shows the block diagram of the controller 64 of FIG. 2. The controller 64 includes a state sequence machine 64C, a minute volume processor 64A and an atrial rate monitor 64B. The minute volume processor 64A uses the data supplied via the internal bus 40 and the bus 22 from the impedance measurement block 42 to relate the minute volume indicated by the impedance measurement to the Metabolic Indicated Rate (MIR). This rate is then used by the machine 64C to vary the length of each interval in the timing cycle. The MIR is also used by the atrial processor 100 to analyze the atrial rhythm. While the pacemaker 10 is preferably operating in a DDDR mode, it should be understood that it can operate in other modes as well. Importantly, in accordance with the present invention, the atrial sense signals are fed to an atrial processor 100 which analyzes the atrial sense signals to determine the amplitude variability of the atrial sense signals and the respective atrial rhythm. Depending on this determination, the processor 100, provides corresponding commands to the state machine 64C. For example, if the processor detects a non-physiological rate and/or rhythm, it generates an AMS on (automatic mode switching) command, in response to which the state machine suspends atrial pacing and performs ventricular pacing independent of the timing of atrial depolarizations until the atrial functions return to normal. When this rate or rhythm is no longer detected the AMS feature is turned OFF.

Figure 4:
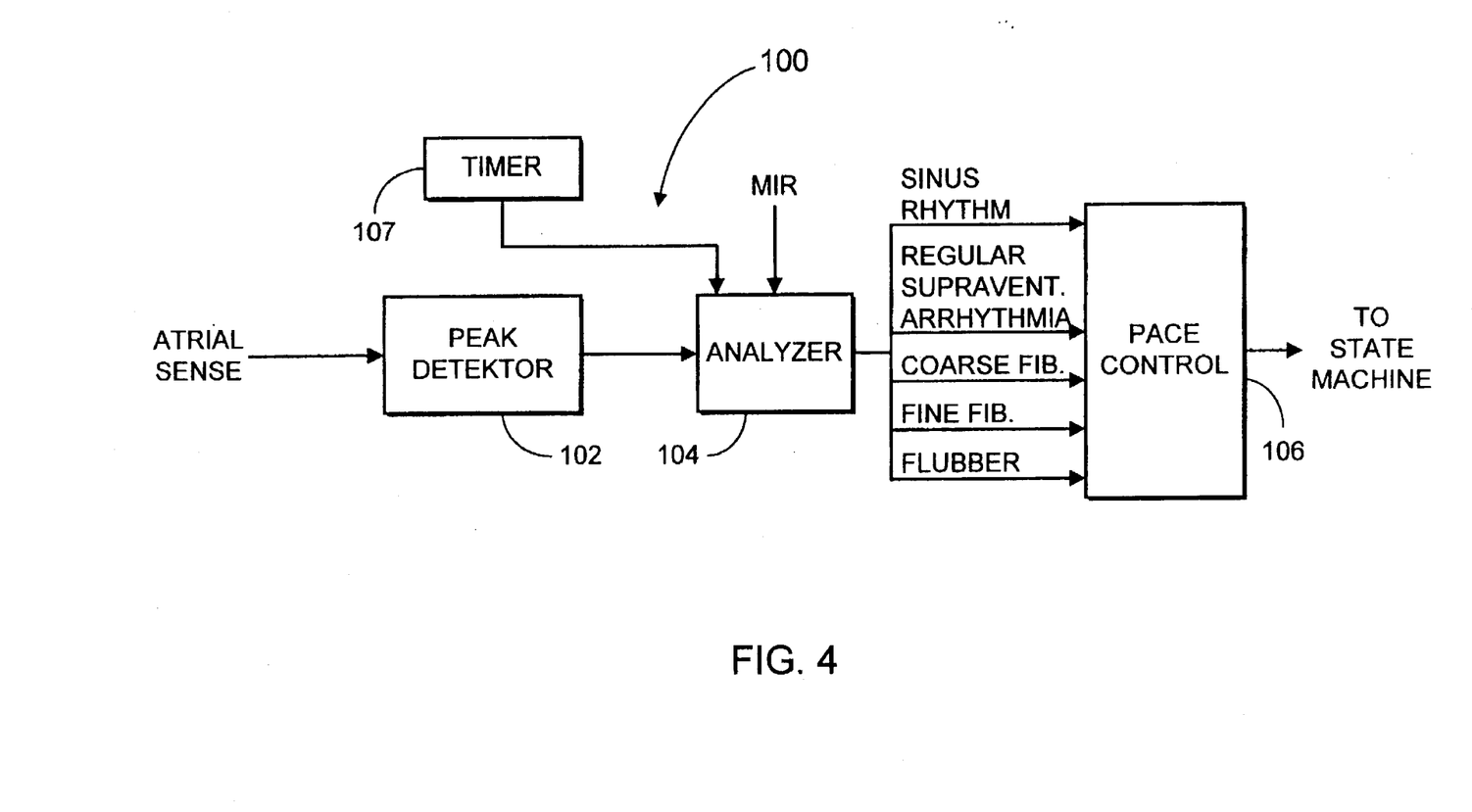
FIG. 4 shows a block diagram of a system used to detect atrial rhythm amplitude stability.

Referring to FIG. 4, in processor 100, the atrial sense signal is fed to a peak detector 102. The peak detector feeds the peak amplitudes of the sensed atrial signals to an analyzer 104. The MIR is also fed into the analyzer 104 from the minute volume processor 64A. The analyzer analyzes these signals as discussed below.

Figure 5A:
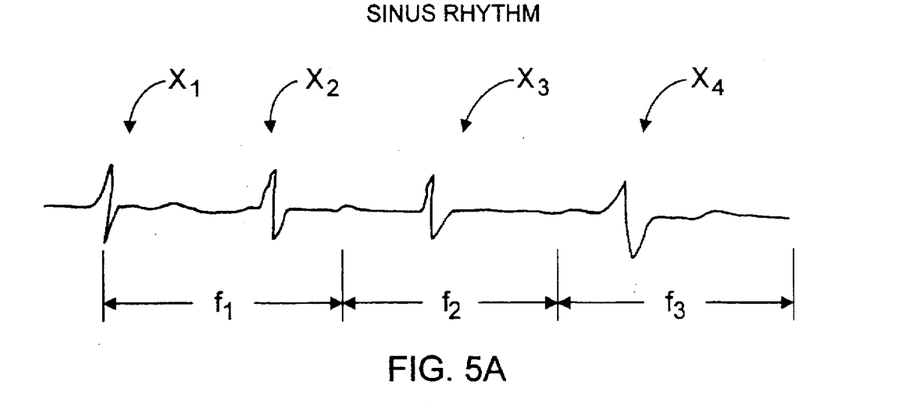
FIGS. 5A, 5B, 5C, 5D, and 5E show atrial signals during sinus rhythm, regular supraventricular arrhythmia, fibrillation/flutter (flubber), coarse fibrillation and fine fibrillation, respectively.
Figure 6A:
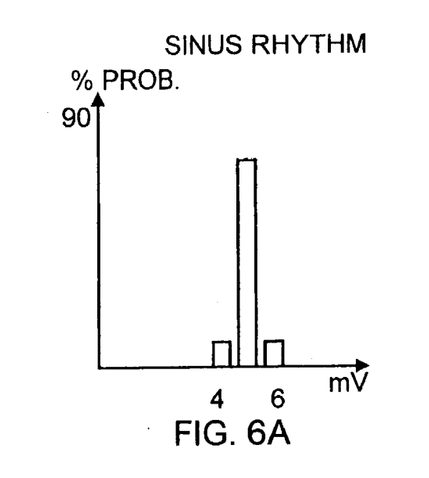
FIGS. 6A, 6B, 6C, 6D, and 6E show amplitude v. frequency of occurrence plots corresponding to the atrial signals of FIGS. 5A, 5B, 5C, 5D, and 5E respectively.
Figure 6B:
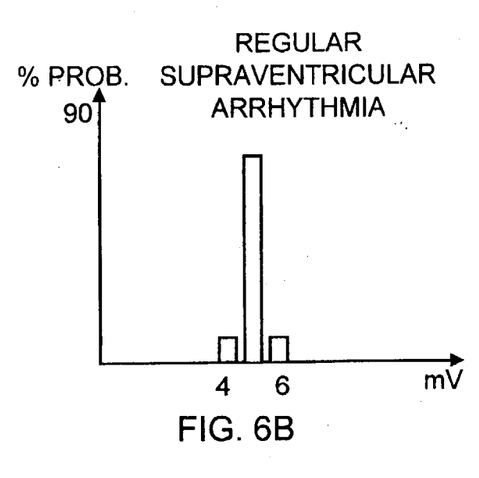

Referring to FIG. 5A, it should be noted that the atrial sense signal sensed during normal sinus rhythm is a well ordered signal having a relatively constant amplitude. That is, if a long-term statistical analysis is performed of the peak value of a large number of atrial sense signals, then, as shown in FIG. 6A, about 90% of the atrial signals will have an amplitude of about 5 mV, about 5% will have an amplitude of about 4 mV and about 5% will have an amplitude of about 6 mV. (It should be understood that the amplitude levels shown in FIGS. 6A–6E and discussed herein are provided for illustrative purposes only, and that the actual values may vary dependent on a large number of factors, including the type of atrial electrodes used, the sensing and amplification circuitry, the cardiac physiology, and so on. In this description, all nominal values refer to signals having an amplitude of the designated range. This value 5 mV refers to signals having an amplitude of 5 mV±0.5 mV.)

Figure 5B:
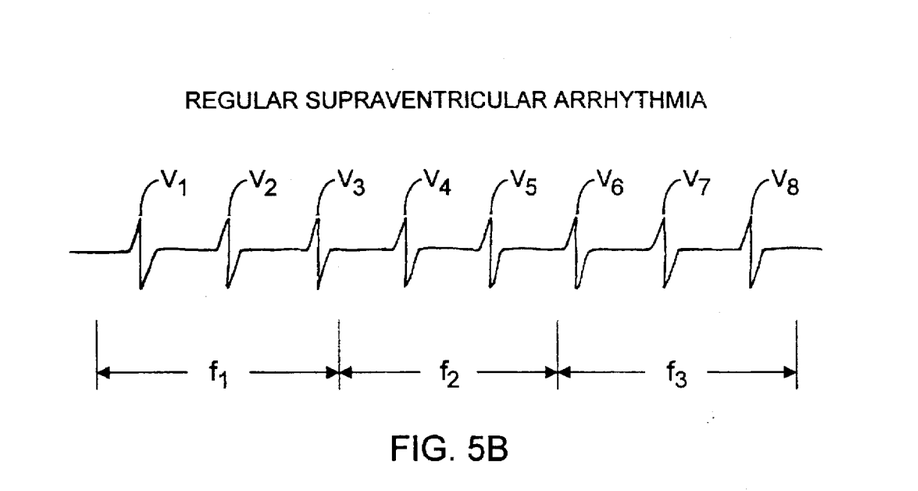

Regular supraventricular arrhythmias (FIG. 5B) typically show a consistent atrial rate and amplitude. The rate is elevated from that during sinus rhythm. In FIG. 5B the atrial rate is approximately 160 beats/min. The atrial amplitude histogram corresponding to this arrhythmia (FIG. 6B) is similar to that during sinus rhythm (FIG. 6A). It would be necessary to include another criteria to distinguish this arrhythmia from sinus rhythm. Here, we use a definition of atrial pathological rate based upon the deviation of actual atrial rate from the metabolic indicated rate or, alternately, a short-term atrial rate.

Figure 5C:
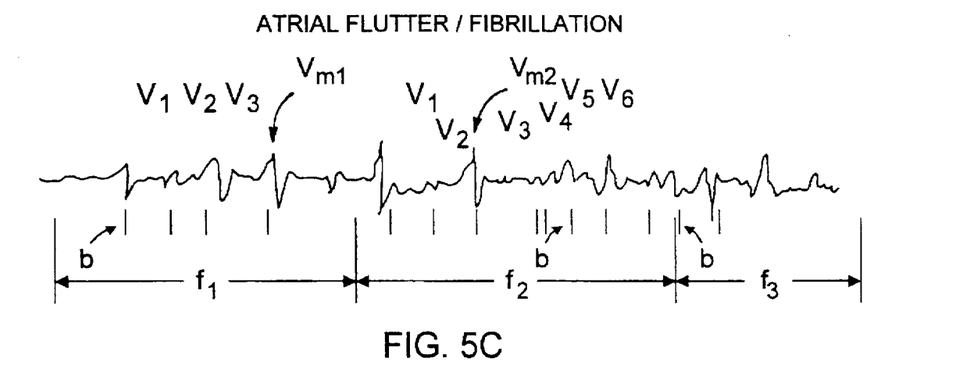
Figure 6C:
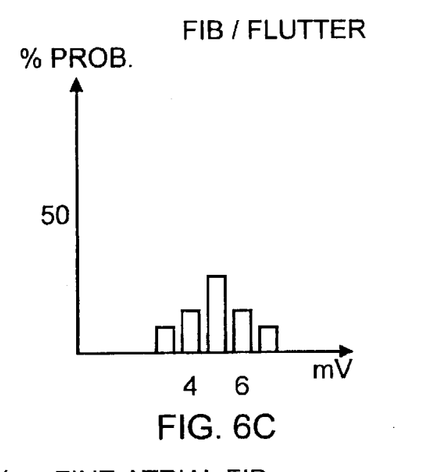

During atrial fibrillation/flutter (rubber) shown in FIG. 5C, the amplitude becomes less organized. For example, as shown in FIG. 6C, typically the amplitude is at the nominal value of 5 mV less than 70% of the time. The remaining sensed signals may range from 3 to 7 mV, as indicated. Thus, the statistical histogram curve has a lower maximum percent and is spread over a broader voltage value.

Figure 5D:
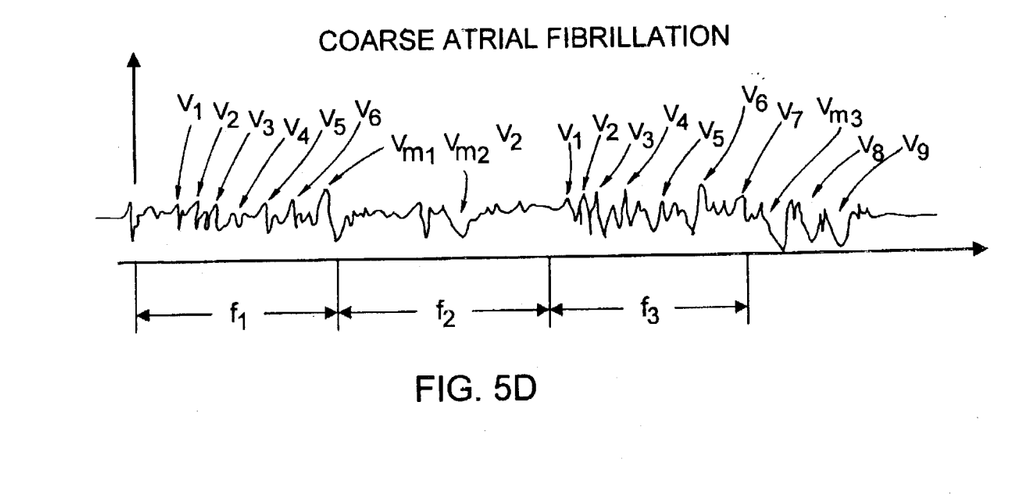
Figure 6D:
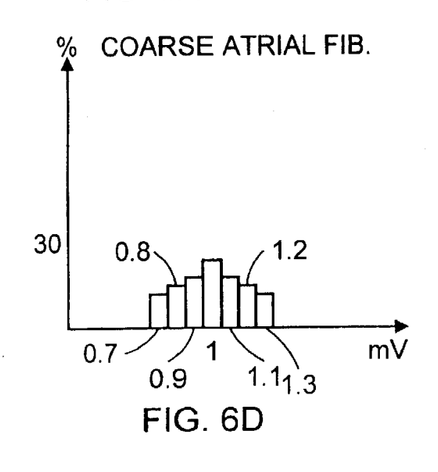

During coarse atrial fibrillation, shown in FIG. 5D, the peak amplitudes become much more disorganized. The example signal in FIG. 6D shows that for this condition, the peak amplitude does not exceed about 1 mV over a comparatively broad voltage range.

Figure 5E:
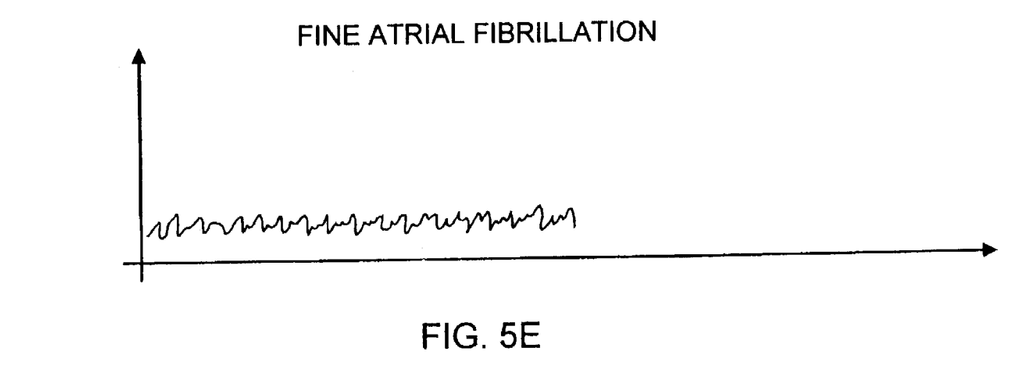
Figure 6E:
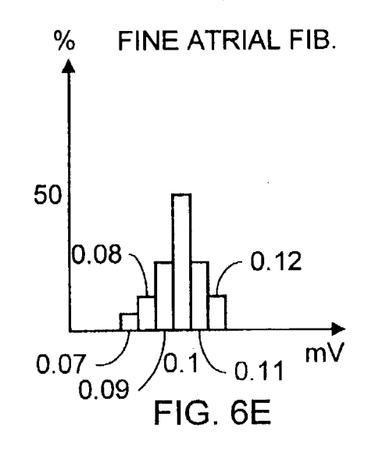

Finally, FIG. 5E shows the atrial sense signals characterizing fine atrial fibrillation. The peak-to-peak amplitudes of these example signals do not much exceed 0.1 mV, as shown in FIG. 6E, but have a relatively narrow voltage range.

Analyzer 104 performs the statistical analysis to determine if the atrial sense signals are indicative of sinus rhythm, regular supraventricular arrhythmia, flubber, coarse fibrillation, or fine fibrillation. This information is then provided to the pace controller 106 for a determination as to whether the state machine needs to adjust its pacing parameters. The information is obtained by defining sequential time periods P, each of which being partitioned into L frames, and analyzing and comparing the atrial senses within each frame, as described below. This timing function is performed by a timer 107.

Analyzer 104 can be implemented a number of ways. Preferably, the atrial amplitude variability is determined by the analyzer from the peak amplitude of each sensed atrial signal. This method is preferable because it can be implemented in a microprocessor by performing only a small number of calculations. The amplitude variability criteria may be combined with a pathological rate criteria. The rate criteria is based on boundary conditions set by the metabolic rate sensor in a rate responsive system, or on allowed deviations from a short term average atrial rate in a non-rate-responsive system.

In order to perform the analysis, consecutive time periods of P seconds, are defined, each time period being partitioned into L time frames having a duration of P/L. Preferably, P/L is defined as the longest pacing interval of the pacemaker, i.e., the default rate used when no atrial signals are sensed. For example, if the default pacing rate is 50 ppm then P/L is 1.2 seconds. Generally, it is believed that P should be about 12 seconds, and therefore L is about 10. Each frame is defined in the following description as j=1 . . . 10.

During this period P an indicia J is derived, said indicia having three terms, as defined in the following formula $$J = I1 + I2 + K$$

The first term, I1, is an indicia of the atrial short term amplitude variability during the 1.2 see frames. The second term, I2, is an indicia of the long-term absolute waveform amplitude change from sinus rhythm. The third term K is added to weigh the indicia J proportionally when the atrial rate is pathological.

Figure 7:
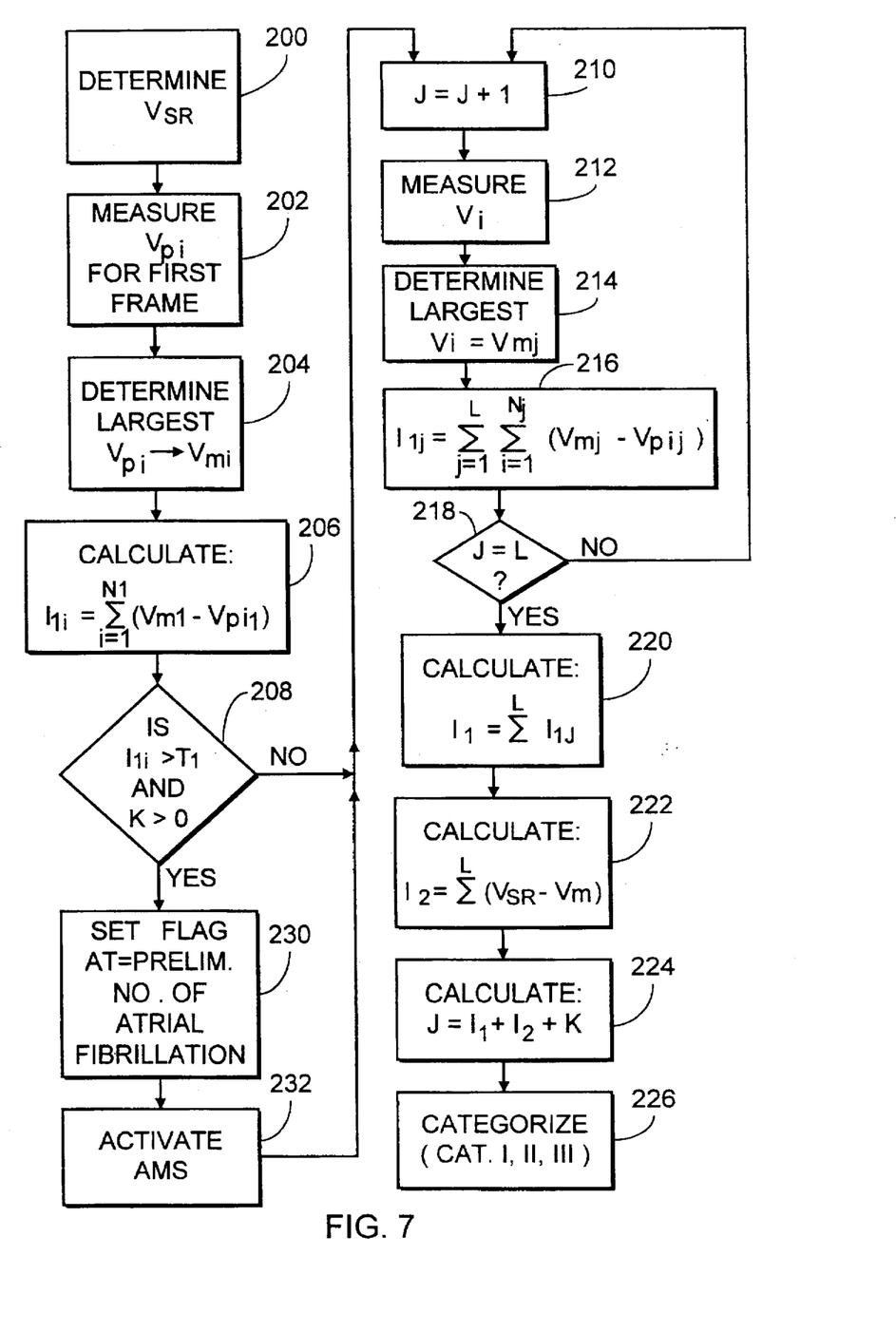
FIG. 7 shows a flow chart for determination of atrial rhythm via atrial waveform amplitude variability.

Details of determining indicia J are shown in FIG. 7. In step 200 while the atrium is known to follow sinus rhythm, a voltage Vsr is determined, where Vsr is the average peak amplitude of a predetermined number (for example 100) of sensed sinus generated atrial signals.

In step 202, all atrial signals in the first frame having a peak amplitude of $$Vp > 0.1 \, Vsr$$

are detected by the peak detector 102. Next, in step 204, the maximum peak amplitude in time frame 1 is defined as Vm1.

The indicia I11 (I1 for the first frame j=1) is calculated in step 206 by using the formula $$I11 = \sum_{i=1}^{N1} (Vm1 - Vpi1)$$

where Vm1 is the frame 1 maximum peak amplitude and Vpi1 are the valid atrial signal peaks (as determined by some preselected criteria) within frame 1. N1 are the total number of peaks in frame 1.

Since the indicia J can be calculated only at the end of period P, e.g., after 12 seconds, a preliminary decision may be made at the end of the first frame. More particularly, as seen in FIG. 7, in step 208 a test is performed to determine if I11 is greater than a threshold level T1 (for example, T1 may be about 5 mV) and K>0. If the determination is 'YES', a preliminary atrial fibrillation flag is set (step 230) and some therapy may be activated (e.g., AMS, step 232). If the determination is 'NO', these two steps are bypassed.

In step 210, the next frame is examined by incrementing the value of j. Next, the peak values Vpi (step 212), the maximum peak values Vmj (step 214), and the terms I1j are determined (step 216) for the next eleven frames. These steps correspond to steps 202, 204, and 206. The more general equation for step 216 is $$I1j = \sum_{j=1}^{L} \sum_{i=1}^{Nj} (Vmj - Vpij)$$

where Vmj is the maximum peak amplitude of within each frame j and Vpij is each valid peak within each frame j. Nj are the total number of peaks within frame j.

In step 220, after all L (e.g., 12) peak values Vpi and all the maximum values Vmj have been calculated ('YES' to step 218), the final value I1 is calculated by summing all L I1j's (step 220).

The second term, I2 (calculated in step 220), is an indicia of the long-term absolute amplitude change. I2 is calculated at the end of each period P using the formula $$I2 = \sum_{j=1}^{L} |Vsr - Vmj|$$

In step 224, the indicia J is calculated and, finally, based on the values of I1, I2, K, and/or J, the atrial condition is categorized (step 226) (i.e., identified as being one of categories I, II, III. Based on these categories, the state sequence machine 64C can provide appropriate therapy, if necessary.

As previously mentioned, the third term K is added to weigh the indicia J when the atrial rate is pathological. The pathological condition of the atrium is determined by the maximum atrial rate appropriate for the persons age and medical condition. Generally, this rate is 220-Age beats/min. The value of K is scaled to appropriately weight the value of J.

The manner in which the indicia J is indicative of the condition of the atrium is now described for each of the categories defined above.

Category I - Sinus Rhythm. FIG. 5A shows a typical atrial signal during an episode of sinus rhythm as might be sensed by an atrial electrode at a rate of 70 beats/min. This signal consists of a plurality of well defined, fairly similar waves such as the four waves X1, X2, X3, X4. The amplitudes of these waves are shown statistically in FIG. 6A as falling mostly in the range of 5 mV. Waves X1 and X2 fall in frame f1 while X3 and X4 fall in frames f2 and f3 respectively. Since the sum of the differences (Vm-Vp) and |Vsr-Vm| for each frame are insubstantial, the terms I1 and I2 are close to zero in this case. The term K is also close to zero because, in this case, the atrium rate is not pathological.

Category II - Regular Supraventricular Arrhythmia. A typical time dependent atrial signal showing this condition is shown in FIG. 5B. As seen in this Figure, all waves are similar in consistency to one another as in Category I. Each peak amplitude Vi is similar to the others. In addition, the peaks are similar in amplitude to Vsr. Therefore, I1 and I2 are close to zero. However, the rate is approximately 160 beats/min, which depending upon the metabolic indicated rate (or alternatively the short-term atrial average rate), may be pathologic. This would result in an increased value for K. It could be set to Vsr or more appropriately scaled, for example. Therefore, low values of I1 and I2 with an increased K indicates a regular supraventricular arrhythmia.

This type of rhythm is normally quite stable and could be an organized rhythm with origin in the atrium, the AV node, or a bypass track to the ventricle. If there is no rate transgression, even with the use of the metabolic sensor as described in previous concepts, then there is no way of determining that it is an arrhythmia and, in any case, will generally be benign to the patient. If there is a rate transgression, pacing will either go into a 'forced synchrony mode' with the intent of keeping the ventricular rate stable and perhaps terminating the arrhythmia. In such a case, AMS would occur after forced synchrony proceeded it for perhaps 10 cycles or forced synchrony would be allowed indefinitely, as long as the Category II rhythm was present.

Category III- Atrial Fibrillation or Fibrillation/Flutter (Flubber): With many types of atrial pathologies, fibrillation and an intermediate between fibrillation and flutter (flubber) is very common. It is known that the nature of this rhythm is such that the amplitude could be any value down to and below 10% of the original signal. The amplitude of the fibrillation waveform is largely dependent on the length of time the rhythm has been present. The expression presented previously will return a value for all states of this rhythm identifying it. If there is amplitude variability and higher rate it will return the appropriate indication of fibrillation or flubber based upon the comparison of J to a threshold value. If the rhythm has deteriorated so that it is often below the sensing threshold it will identify this situation by extending the standby or minimum rate and noting: 1) the difference to the sinus rhythm amplitude is high (increased I2 due to the absence of intrinsic atrial signals), and 2) occasionally the amplitude variability is high (increased I1). One issue is to eliminate the effect of frequent PACs (premature atrial contractions), which could be misread as an arrhythmia. In such a case the arrhythmia threshold would be set appropriately to distinguish sinus rhythm with PACs versus atrial fibrillation. In the PAC case the size of the first I1 and I2 terms would be larger than for sinus rhythm, but not large enough to signal atrial fibrillation.

In FIG. 5D the atrial senses have amplitudes Vi, with Vmj indicating the largest such signal within each frame. These values are then substituted into the relationships given above as follows. The waveform peaks, Vi, in the first frame are. The subsequent terms in the same frame are 0.4, 0.6, 0.3, 0.6, 0.7, 0.7 mV, 1 mV. Therefore, Vm1 equals 1 mV which yields a value of 2.2 mV for I11. The nine remaining frames are then summed over the next 10.8 seconds and summed with I11 to yield an I1 of 20.5 Mv. A calculation for I2 over the ten frames yields I2=30.2 Mv. K is scaled to a value of 5.0. Therefore, J=I1+K2+K=20.5+30.2+5.0=55.7.

Similarly, in the case of very fine fibrillation (FIGS. 5E and 6E) pacing it is important to note that it is possible that a low sensed atrial rate could cause K to become lower than the threshold for pathological rhythms because of under-sensing the fine atrial fibrillatory waveforms. In such a case, pacing could occur at the minimal rate. This would cause the value of Vmj's to frequently be zero and hence I2 would become large. If no fibrillatory waves were sensed in the 10 frames, I2 would increase to 10×Vsr or approximately 50 mV (assuming Vsr=5.0 mV). I1 might also increase from zero if a small number of the fine waveform peaks are sensed. To enable this test to be maximally effective, the standby or minimum rate is always set to the minimum practical level, e.g., to 50 ppm, which is an unlikely low rate for the atrium.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable pacemaker comprising:

at least one atrial sensor for sensing atrial signals;

a ventricular sensor for sensing ventricular signals;

a pacing generator for generating at least one of a ventricular and atrial pacing signals in accordance with a command signal;

an atrial processor receiving said atrial signals, said atrial processor including an analyzer for determining peak amplitudes of said atrial signals and a normal sinus rhythm value of said peak amplitudes, and for determining a change in a variability and deviation of said normal rhythm value, said atrial processor being further provided to detect new state of the atrium by analyzing said change in variability and deviation of said normal sinus rhythm value;

a controller receiving indication of said atrial and ventricular signals and said new atrial state and generating in response said command signal on the basis of said new atrial state.

2. The pacemaker of claim 1 wherein said analyzer further includes a categorizer for categorizing said new atrial state as one of a normal sinus rhythm, coarse fibrillation, fine fibrillation and flubber state.

3. The pacemaker of claim 2 further comprising a metabolic indicated rate parameter processor for generating a metabolic indicated rate parameter, said controller receiving said metabolic indicated rate parameter to modify an output of said categorizer.

4. The pacemaker of claim 2 wherein said atrial signals have a sinus rhythm and said analyzer includes a first portion for determining a short term variability and deviation of an amplitude of said atrial signals and a second portion for determining a long term variation of said atrial signals with respect to said sinus rhythm, said portions generating respective first and second indicia, said categorizer generating said atrial state based on a combination of said indicia.

5. The pacemaker of claim 4 wherein said analyzer includes a timer for defining sequential time periods, each period being partitioned into frames, wherein said first indicia is determined for each frame and said second indicia is determined for each period.

6. An implantable pacemaker comprising:

an atrial sensor for sensing atrial signals, said atrial signals having peak amplitudes and including sinus rhythm atrial signals and non-sinus rhythm atrial signals;

a ventricular sensor for sensing ventricular signals;

a first analyzer for determining a short term variability and deviation of said non-sinus rhythm signals from said sinus rhythm atrial signals and for generating a first indicia, said first indicia being dependent on said short term peak amplitude variability and deviation;

a second analyzer for determining a long term variability of said atrial signals and for generating a second indicia, said second indicia being dependent on said long term variability;

a categorizer for categorizing a new state of the atrium as a pathological state by combining said first and second indicia;

a pulse generator for generating atrial and ventricular pulses in response to a command signals; and a controller for generating said command signals in response to said atrial and ventricular signals and said new state of the atrium.

7. The pacemaker of claim 6 further comprising a timer for generating sequential time periods, each time period being partitioned into several time frames, wherein each said first indicia is determined from atrial signals sensed during one of said frames, and each second indicia is determine during one of said periods.

8. The pacemaker of claim 6 further comprising a metabolic sensor for sensing a metabolic demand parameter, said controller generating said command signals in accordance with said metabolic demand parameter.

9. The pacemaker of claim 8 further including a mode switcher for switching said controller between a first mode in which said pulses are generated at a rate dependent on said metabolic rate parameter and a second mode in which said pulses are generated independently of said metabolic rate parameter.

10. The pacemaker of claim 9 wherein said mode switcher is activated by said new atrial state.

11. In an implantable pacemaker of the kind having atrial and ventricular sensors for sensing atrial and ventricular events and a pulse generator for generating atrial and ventricular events and a pulse generator for generating atrial and ventricular pulses on demand, a method of classifying cardiac arrhythmia from said atrial events comprising the steps of:

sensing a predetermined number of atrial events and generating corresponding atrial signals;

measuring an amplitude of each of said atrial signals;

determining a short term variability and deviation of said amplitudes;

determining a long term variability and deviation of said amplitudes;

generating a first indicative of said short term variability and deviation of said amplitudes;

generating a second indicia indicative of said long term variation and deviation of said amplitudes;

combining said first and second indicia into a third indicia; and categorizing said cardiac arrhythmia in accordance with said third indicia.

12. The method of claim 11 further comprising the steps of:

defining a plurality of sequential periods, each period consisting of several frames;

measuring said first indicia during said frames; and measuring said second indicia during said periods.

13. The method if claim 12 wherein each said period is about 12 seconds and each said frame is about 1.2 secs.

14. The method of claim 12 further comprising selecting said frames to include several cardiac cycles.

15. The method of claim 11 further comprising categorizing a cardiac state as being one of a flutter/flubber, coarse atrial fibrillation and fine atrial fibrillation.

16. The method of claim 11 comprising the steps of:

generating a metabolic demand parameter after said step of categorizing; and generating said pacing pulses at one of a first rate and a second rate wherein said first rate is related to said demand parameter and said second rate is a fixed rate independent of said demand parameter.

17. The method of claim 16 further comprising switching between said first and second rate in response to said categorization of said atrial state.

* * * * *